United States Patent [19]

Batt et al.

[11] Patent Number: 5,707,844
[45] Date of Patent: Jan. 13, 1998

[54] IMMUNOASSAY REAGENTS AND METHODS FOR DETECTING BREQUINAR AND ANALOGS

[75] Inventors: Douglas Guy Batt, Wilmington; William Galbraith, Newark; Paul Moore Simon, Wilmington, all of Del.

[73] Assignee: The DuPont Merck Pharmaceutical Company, Wilmington, Del.

[21] Appl. No.: 372,472

[22] Filed: Jan. 13, 1995

Related U.S. Application Data

[62] Division of Ser. No. 72,641, Jun. 8, 1993, Pat. No. 5,393,891.

[51] Int. Cl.$^6$ ............ C12N 9/96; A61K 39/385; C07D 215/20

[52] U.S. Cl. ............ 435/188; 530/363; 530/367; 530/395; 530/807; 546/170; 436/546; 436/800; 424/193.1; 514/453; 514/462; 514/54

[58] Field of Search ............ 546/170; 435/188; 530/363, 367, 395, 807; 424/193.1; 436/546, 800; 514/453, 462, 54

[56] References Cited

U.S. PATENT DOCUMENTS 3,812,123  5/1974  Otterstedt et al. ............ 546/88
5,393,891  2/1995  Batt et al. ............ 546/170

FOREIGN PATENT DOCUMENTS

| 0133244   | 2/1985 | European Pat. Off. . |
| 0379145   | 7/1990 | European Pat. Off. . |
| 2601141   | 1/1988 | France . |
| 2252161   | 7/1992 | United Kingdom . |
| WO94 03807 | 2/1994 | WIPO . |
| WO94 03811 | 2/1994 | WIPO . |

OTHER PUBLICATIONS

Hasegawa, T. et al., *J. Toxicological Sci.*, 11, pp. 313–319, (1986).

*Primary Examiner*—Leon B. Lankford, Jr.
*Assistant Examiner*—Francisco C. Prats

[57] ABSTRACT

The present invention is directed to immunoassay reagents including specific antibodies to quinoline carboxylic acids, such as brequinar; novel quinoline carboxylic acid haptens useful as standards in immunoassays or for conjugating to large molecular weight carriers as immunogens or conjugating to detectable fluorescent moieties as tracer compounds. The present invention also relates to immunoassays for detecting quinoline carboxylic acids in clinical samples, and finally to kits containing said reagents.

20 Claims, No Drawings

IMMUNOASSAY REAGENTS AND METHODS FOR DETECTING BREQUINAR AND ANALOGS

This is a division of application Ser. No. 08/072,641, filed Jun. 8, 1993, now U.S. Pat. No. 5,393,891.

FIELD OF THE INVENTION

This invention relates to antibodies and other reagents, to immunoassays, and to kits containing the reagents for determining the presence of quinoline carboxylic acids, including brequinar, in a test sample.

BACKGROUND OF THE INVENTION

Brequinar is a quinoline carboxylic acid described in U.S. Pat. No. 4,680,299, issued Jul. 14, 1987. The term "brequinar" as used herein and in the claims refers to brequinar sodium, which is the compound 2-(2'-fluoro-1,1'-biphenyl-4-yl)-6-fluoro-3-methyl-4-quinoline-carboxylic acid, sodium salt, or other suitable salts or free acidss thereof, and has the formula:

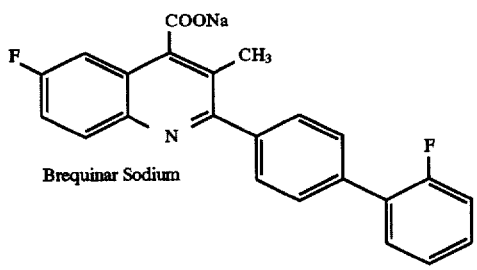

Brequinar Sodium

Said quinoline carboxylic acids are potent inhibitors of dihydroorotate dehydrogenase (DHO-DH), the fourth enzyme in the de novo pyrimidine biosynthetic pathway. A structure activity relationship for the inhibition of DHO-DH by the quinoline carboxylic acids has been developed, S-F. Chen et al., Biochem. Pharmacol. 40:709-714 (1990). The effect of the DHO-DH inhibition by the quinoline carboxylic acids is to deplete the plasma uridine concentrations in animals and patients, G. J. Peters et al., Cancer Res. 50:4644-4649 (1990). Said quinoline carboxylic acids were shown to be useful as tumor inhibiting agents (U.S. Pat. No. 4,680,299) and also have been shown to be anti-inflammatory agents (U.S. Pat. No. 4,861,783).

Recently, brequinar was shown to be a potent immunosuppressive agent in vivo to prevent the rejection of transplanted organs (U.S. Pat. No. 4,968,701) with the capability of suppressing 1) mouse heart allograft rejection, M. P. Murphy and R. E. Morris, Med. Sci. Res. 19:835-836 (1991), 2) rat heart, liver, and kidney allograft rejection, D. V. Cramer et al., Transplantation 53:303-308 (1992), and 3) hamster-to-rat-cardiac xenografts, D. V. Cramer et al., Transplantation Proc. 24:720-721 (1992). Brequinar is currently undergoing clinical trials for the prevention of graft rejection in transplant patients. Moreover, it has been determined that an analog of brequinar, 2-(1,1'-biphenyl-4-yl)-5-chloro-3-methyl-4-quinolinecarboxylic acid, sodium salt, which was also described in U.S. Pat. No. 4,680,299, issued Jul. 14, 1987, is also active as an immunosuppressive agent.

The compound, 2-(2'-fluoro-4'-hydroxy-1,1'-biphenyl-4-yl)-6-fluoro-3-methyl-4-quinoline-carboxylic acid, sodium salt, was the primary metabolite identified from patients treated with brequinar. It was determined that this hydroxyl-metabolite is pharmacologically inactive as an immunosuppressive agent.

While a certain level of brequinar or other active quinoline carboxylic acids must be maintained in the bloodstream to prevent rejection of transplanted organs, distribution and metabolism of these compounds can vary between individuals as well as between measurements within a single individual during the course of therapy. Accordingly, it is important to monitor the level of quinoline carboxylic acids in biological fluids in a rapid and convenient manner to maintain and adjust dosage for proper pharmacodynamics in transplant patients. Measuring brequinar and other active quinoline carboxylic acids in clinical samples from patients is an important tool to enable one to assure maximum efficacy of the drug. Such measurement in samples could potentially be complicated by the presence of inactive metabolites of quinoline carboxylic acids therein, such as the inactive hydroxyl-metabolite mentioned above. Therefore, it is also desirable to be able to measure brequinar or other quinoline carboxylic acids independently from any inactive metabolites thereof. This invention is directed to antibodies and other reagents, immunoassays and diagnostic kits useful for the measurement of quinoline carboxylic acids present in biological fluids from patients treated with said quinoline carboxylic acids.

Immunoassays are often used for therapeutic drug monitoring because of their rapidity, convenience and sensitivity. In particular, the immunosuppressant, cyclosporine A, is widely monitored using a variety of immunoassays, U. Kunzendorf et al., Klin Wochenschr 67:438-441 (1989) and B. Tjandra-Maga et al., J.Clin Chem Clin Biochem 28:53-57 (1990). EPO Application No. 473,961 (Morrison, et al.) describes immunoassay reagents and a method for determining cyclosporine in test samples. Presently, brequinar is measured by high performance liquid chromatography, which is very costly and time-consuming. Nevertheless, there remains the need for specific high affinity reagents and immunoassays to quickly and acurately measure quinoline carboxylic acid levels, including brequinar, in patients. The present invention is directed to addressing these, as well as other, important needs.

SUMMARY OF THE INVENTION

An embodiment of the present invention is directed to hybridoma cell lines capable of producing monoclonal antibodies to quinoline carboxylic acids (QCA) including pharmacologically active QCAs of Formula II which includes brequinar. QCAs of Formula II are of the formula:

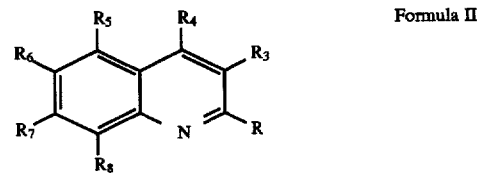

Formula II wherein

R is

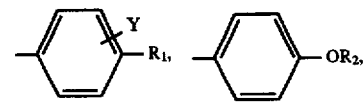

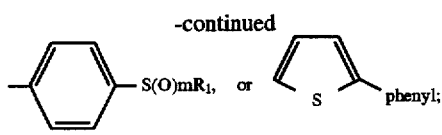

$R^1$ is cyclohexyl,

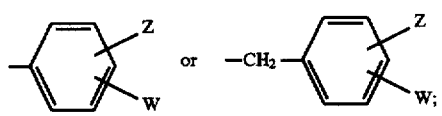

$R^2$ is

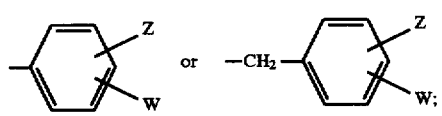

$R^3$ is H, alkoxy of 1–3 carbons or alkyl is 1–2 carbons;
$R^4$ is $CO_2H$ or $CO_2R^{11}$;
$R^5$, $R^6$, $R^7$, $R^8$ are independently H, F, Cl, Br, I, $CH_3$, $CF_3$, $SCH_3$, or $CH_2CH_3$, at least two of $R^5$, $R^6$, $R^7$, and $R^8$ being H;
$R^9$ and $R^{9A}$ are independently H or alkyl of 1–3 carbons;
$R^{11}$ is $(CH_2)_{2-4}NR^9R^{9A}$;
W, Y, and Z are independently H, F, Cl, Br, alkyl of 1–5 carbons, $NO_2$, $CF_3$, or $OCH_3$;
m is 0 or 1;
or a pharmaceutically suitable salt thereof.

Another embodiment of this invention is the monoclonal antibodies produced by said hybridomas. Said monoclonal antibodies are capable of specifically binding to at least one antigenic determinant of a QCA. A further object of the invention relates to monoclonal antibodies which are highly specific to brequinar, that is these antibodies specifically bind to brequinar and are substantially non-reactive with inactive hydroxyl-metabolites thereof. The phrase "substantially non-reactive" as used herein and in the claims means said antibodies bind to less than 1% of the amount of inactive hydroxyl metabolite present in the sample.

The phrase "pharmacologically active" as used herein and in the claims means compounds active as inhibitors of dihydroorotate dehydrogenase which are useful as immunosuppressive agents, anti-inflammatory agents or anti-tumor agents, and includes compounds of formula II. Specifically a pharmacologically active analog of brequinar is the compound: 2-(1,1'-biphenyl-4-yl)-5-chloro-3-methyl-4-quinolinecarboxylic acid, sodium salt, (hereinafter denoted "analog"). The term "inactive metabolite" as used herein and in the claims refers to a metabolite of a pharmacologically active QCA which does not have immunosupressive activity, such as the identified hydroxyl-metabolite of brequinar, 2-(2'-fluoro-4'-hydroxy-1,1'-biphenyl-4-yl)-6-fluoro-3-methyl-4-quinoline-carboxylic acid, sodium salt. As stated above, this was the primary metabolite of brequinar identified in humans and which is pharmacologically inactive as an immunosuppressive agent. The term "hapten" as used herein and in the claims refers to a quinoline carboxylic acid of Formula (I) (below) useful for conjugation to other molecules.

In addition, another embodiment is directed to polyclonal antibodies (as antisera, purified IgG, or affinity purified antibodies) which are capable of specifically binding to at least one antigenic determinant of quinoline carboxylic acids. Such polyclonal and monoclonal antibodies are useful as immunoassay-reagents for measuring quinoline carboxylic acids, such as brequinar, in fluid samples in any patient treated with such for purposes including inhibiting tumor growth or psoriasis or inhibiting rejection of any type of transplanted tissue.

Further embodiments of the present invention are immunoassays for detecting the presence of quinoline carboxylic acids including brequinar in fluids; such immunoassays comprising contacting fluid of the patient, such as urine, whole blood, serum, or plasma, with a monoclonal or polyclonal antibody of the invention and screening for quinoline carboxylic acid-antibody interactions. Such immunoassays are known in the art and include, but are not limited to radioimmunoassays (RIAs), enzyme-linked immunosorbent assays (ELISAs), fluorescent immunoassays, and fluorescence polarization immunoassays (FPIAs), for example as described in EPO Applications 473,961 and 283,801 which are hereby incorporated by reference in their entirety.

Another embodiment includes diagnostic kits comprising all of the essential reagents required to perform a desired immunoassay according to the present invention. The diagnostic kit may be presented in a commercially packaged form as a combination of one or more containers holding the necessary reagents. Such a kit may comprise a quinoline carboxylic acid, such as but not limited to compounds of Formula (II) including brequinar, or a hapten of Formula (I) to be used as a standard control measurement and a monoclonal or polyclonal antibody of the present invention in combination with conventional diagnostic kit components. Said kits may also contain haptens conjugated to a detectable fluorescent moiety, an enzyme or biotin for use as "tracer compounds" in fluorescence immunoassays or said kits may contain haptens conjugated to high molecular weight carrier molecules, referred to as "immunogens". Both types of said hapten-conjugated molecules, that is tracer compounds, and immunogens are embodiments of this invention and are discussed further below. Conventional diagnostic kit components will be readily apparent to those skilled in the art and are disclosed in numerous publications, including *Antibodies A Laboratory Manual* (E. Harlow, D. Lane, Cold Spring Harbor Laboratory Press, 1989), the disclosures of which are hereby incorporated by reference in their entirety. Conventional diagnostic kit components may include such items as, for example, microtitre plates, buffers, such as EDTA buffer, Tris buffer, secondary buffers, such as peroxidase conjugated anti-mouse IgG or anti-rabbit IgG, and other standard reagents and components (anti-IgG to the animal from which the first antibody was derived). Particularly preferred is a diagnostic kit for the fluorescent polarization immunoassay determination of quinoline carboxylic acids such as brequinar, comprising an appropriate fluorescent tracer compound of the present invention, an appropriate antibody reagent of the present invention, a precipitation reagent (such as ammonium acetate and isopropanol) and other conventional materials.

Further, the instant invention provides novel quinoline carboxylic acid compounds useful as haptens of pharmacologically active QCAs, consisting of a hapten of Formula (I):

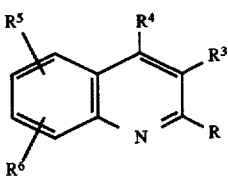

wherein:

R is

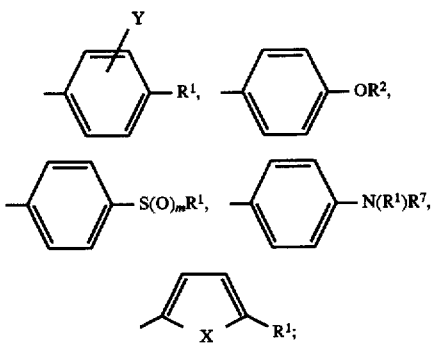

X is O, S, NR$^7$ or CH=N;

R$^1$ is alkyl of 5–12 carbon atoms, alkenyl of 5–12 carbon atoms, cycloalkyl of 3–7 carbon atoms, cycloalkylalkyl of 5–12 carbon atoms, phenyl substituted with 0–3 Y, or benzyl substituted with 0–3 Y;

R$^2$ is phenyl substituted with 0–3 Y, or benzyl substituted with 0–3 Y;

R$^3$ is H, alkoxy of 1–3 carbon atoms, alkylthio of 1–3 carbon atoms, or alkyl of 1–2 carbon atoms;

R$^4$ is COOH;

R$^5$ is H, F, Cl, Br, I, CH$_3$, CF$_3$, S(O)$_n$R$^8$ or ethyl;

R$^6$ is (CR$^9$R$^{10}$)$_p$CH$_2$NH$_2$;

R$^7$, R$^8$, R$^9$ and R$^{10}$ are independently H or alkyl of 1–3 carbon atoms;

Y is selected independently at each occurrence from the group consisting of: H, F, Cl, Br, alkyl of 1–5 carbon atoms, NO$_2$, alkoxy of 1–5 carbon atoms, alkylthio of 1–5 carbon atoms, OH, CF$_3$ and NH$_2$;

m and n are independently 0, 1 or 2; and p is 0–12;

or a suitable salt thereof.

Preferred haptens are those haptens of formula I wherein:

R is para-phenylene;

R$^1$ is cycloalkyl of 3–7 carbon atoms; phenyl optionally substituted with hydroxyl; phenyl substituted with one halogen, alkyl of 1–5 carbon atoms or CF$_3$ and also optionally with one hydroxyl; phenoxy; or phenoxy substituted with one halogen or alkyl of 1–5 carbon atoms;

R$^3$ is H, alkyl of 1–2 carbon atoms, or methylthio;

R$^5$ is H, halogen, CH$_3$ or CF$_3$; and p is 1–12;

or a suitable salt thereof.

More preferred haptens are those haptens of formula I wherein:

R$^1$ is cyclohexyl, phenyl, hydroxyphenyl, fluorophenyl, fluorohydroxyphenyl, or methylphenyl;

R$^5$ is hydrogen; and

R$^6$ is (CH$_2$)$_p$NH$_2$, and is located at the 6-position of the quinoline ring and p is 2–8; or a suitable salt thereof.

Specifically preferred are the following haptens of formula I:

2-(2'-Fluoro-1,1'-biphenyl-4-yl)-3-methyl-6-(2-aminoethyl)-4-quinolinecarboxylic acid;

2-(2'-Fluoro-1,1'-biphenyl-4-yl)-3-methyl-6-(2-aminoethyl)-4-quinolinecarboxylic acid, sodium salt;

2-(2'-Fluoro-4'-hydroxy-1,1'-biphenyl-4-yl)-3-methyl-6-(2-aminoethyl)-4-quinolinecarboxylic acid; and 2-(2'-Fluoro-4'-hydroxy-1,1'-biphenyl-4-yl)-3-methyl-6-(2-aminoethyl)-4-quinolinecarboxylic acid, sodium salt.

Haptens of Formula (I) find many uses, including but not limited to the following: they may be either conjugated with a high molecular weight carrier molecule to provide antigenicity for raising antibodies; conjugated with a detectable labeling moiety, an enzyme or biotin to use as tracer compounds in an immunoassay; or used as a standard control in an immunoassay for comparing against quinoline carboxylic acid measurements from a test sample. The term "conjugate" or any form thereof as used herein and in the claims means the mechanism or act of covalently linking two molecules.

A further embodiment is directed to said tracer compounds as discussed above. The term "tracer compound" as used herein and in the claims refers to a quinoline carboxylic acid, such as but not limited to compounds of Formula (II), including brequinar, or a hapten of Formula (I) that is conjugated to a detectable fluorescent moiety, an enzyme or biotin. The detectable moiety component may be selected from a variety of detectable labels known in the art including, but not limited to, chemiluminescent molecules, luminescent molecules such as fluorescein and fluorescein analogs, enzymes and the like. According to the present invention, fluorescein and fluorescein analogs are preferred, such as aminomethylfluoresceins, carboxyfluoresceins and fluoresceinamines wherein such fluorescent tracer compounds are particularly useful for performing fluorescent polarization immunoassays.

An embodiment of the present invention is also directed to creating immunogenic characteristics of QCAs, including brequinar, by making immunogens comprised of any of the above novel haptens of Formula (I) conjugated to a suitable high molecular weight carrier molecule. Such immunogens are capable of causing an immune reaction and thereby raising antibodies in an animal. The term "immunogens" as used herein and in the claims refers to the structure comprised of one or more of haptens of Formula (I) covalently linked to a suitable high molecular weight carrier molecule. Such high molecular weight carrier molecules may include but are not limited to proteins, polysaccharides, and various latex particles. Said proteins include bovine serum albumin, ovalbumin, and keyhole limpet hemocyanin. Specifically preferred immunogens include 2-(2'-Fluoro-1,1'-biphenyl-4-yl)-3-methyl-6-(2-aminoethyl)-4-quinolinecarboxylic acid, sodium salt conjugated to the primary amino groups of bovine serum albumin (BSA); 2-(2'-Fluoro-1,1'-biphenyl-4-yl)-3-methyl-6-(2-aminoethyl)-4-quinolinecarboxylic acid, sodium salt conjugated to the primary amino groups of keyhole limpet hemocyanin (KLH); 2-(2'-Fluoro-1,1'-biphenyl-4-yl)-3-methyl-6-(2-aminoethyl)-4-quinolinecarboxylic acid, sodium salt conjugated to the primary amino groups of ovalbumin (OA); and 2-(2'-Fluoro-4'-hydroxy-1,1'-biphenyl-4-yl)-3-methyl-6-(2-aminoethyl)-4-quinolinecarboxylic acid, sodium salt conjugated to the primary amino groups of BSA

DETAILED DESCRIPTION OF THE INVENTION

Conjugation can be obtained in various fashions, as will be apparent to those skilled in the art, and many such methods are described in the following examples and also described in *Chemistry of Protein Conjugation and Cross-Linking*, S. Wong, CRC Press, Inc. which is hereby incorporated by reference in its entirety. Basically it involves covalently linking a hapten of Formula (I) through a coupling group (such as the $NH_2$ group of $R^6$ of the haptens of Formula I) to either a detectable fluorescence moiety (for tracer comounds) or a suitable high molecular weight carrier molecule (for an immunogen) under conditions normally used to form amide bonds or other suitable bonds, such as a Schiff's base.

The hybridomas and monoclonal antibodies of the invention may be obtained by any conventional method or by the methods described in the following examples. In general, an animal (a wide range of vertebrate species can be used, the most common being mice, rats, guinea pigs, hamsters, and rabbits) is immunized with an immunogen emulsified in an adjuvant such as Complete or Incomplete Freund's Adjuvant, aluminum hydroxide, or any agent that would aid in enhancing the immunogen's effectiveness, and boosted at regular intervals. The animal serum is assayed for the presence of the desired antibody by any convenient method, frequently an ELISA or RIA as described in *Laboratory Techniques in Biochemistry and Molecular Biology*, Volume 6, part 2, Elsevier, 1987, which is hereby incorporated by reference in its entirety. When an acceptable titer of antibody is detected, such as 1:500 or greater, the animal is euthanized and the spleen is aseptically removed for fusion. The spleen cells are mixed with a specially selected immortal myeloma cell line, such as Sp2/0-Ag14 or NS1 cell lines, and the mixture is then exposed to an agent, typically polyethylene glycol or the like, which promotes the fusion of cells. Under these circumstances fusion takes place in a random selection and a fused cell mixture together with unfused cells of each type is the resulting product. The myeloma cell lines that are used for fusion are specifically chosen such that, by the use of selection media, such as HAT: hypoxanthine, aminopterin, and thymidine, the only cells to persist in culture from the fusion mixture are those that are hybrids between cells derived from the immunized donor and the myeloma cells.

After fusion, the cells are diluted and cultured in the selective media. They may be supplemented with growth factors, such as IL-6 or insulin, to enhance the formation and growth of the hybridomas. When sufficient cell growth has occurred, the spent culture supernatant is tested by any convenient means, including an ELISA or RIA, for presence of antibody which has pre-determined specificity towards the chosen immunogen. Those cultures containing the antibody of choice are cloned by limiting dilution until it can be adduced with certainty that the cell culture is single cell (monoclonal) in origin; all cells present synthesize an identical antibody gene product. Monoclonal antibody preparations from these cells exhibit reactivity with the single immunogenic determinant. In addition, the preparation of hybridomas and monoclonal antibodies is described, for example in *Antibodies A Laboratory Manual* (E. Harlow, D. Lane, Cold Spring Harbor Laboratory Press, 1989), the disclosures of which are hereby incorporated by reference in their entirety.

Polyclonal antibodies to the subject immunogens are also provided in the present invention. Such polyclonal antibodies may be produced using standard techniques, for example immunizing an animal with the emulsified immunogen, as described above, removing the serum from the animal and then harvesting the resultant polyclonal antibodies from the serum. If desired, the polyclonal antibodies may be used as an IgG fraction or may be further purified in varying degrees. Procedures for preparing, harvesting and purifying polyclonal antibodies are well known in the art, and are described, for example in *Methods In Enzymology: A Laboratory Text for Instruction and Research* (Garvey, et.al., 3rd. ed., Chapters 22, 24–30; W. A. Benjamin Inc., 1977), the disclosures of which are hereby incorporated by reference in their entirety.

As will be apparent to one skilled in the art, the amount of monoclonal and/or polyclonal antibody of the present invention in any diagnostic immunoassay may vary. By way of general guidance, the monoclonal and/or polyclonal antibody should be present in an amount sufficient to permit significant binding to quinoline carboxylic acids, including brequinar, present in a fluid sample. As those skilled in the art will recognize, an amount between about 0.1 to about 5 µg antibodies per ml of fluid is generally suitable, although larger or smaller amounts of antibodies may also be used.

The invention also contemplates diagnostic kits comprising all of the essential reagents required to perform a desired immunoassay according to the present invention. Using the kit components, a sample of the patient's bodily fluid, such as whole blood or portions or partitions thereof, or urine, could be tested in an immunoassay using the antibodies of the present invention and can be compared with the results of a similar test which employs a QCA, such as those of Formula (II) which includes brequinar or a hapten of Formula (I) as a standard.

The present invention is further described in the following examples. These examples are not to be construed as limiting the scope of the appended claims.

Synthesis of the Haptens

The haptens of present invention may be prepared using known methods by one skilled in the art. A particularly useful method is the Pfitzinger condensation, as described for example in Hesson, U.S. Pat. No. 4,680,299, which is hereby incorporated by reference in its entirety, wherein an appropriately substituted isatin analog 2 and an appropriately substituted ketone 3 are allowed to react, in an appropriate reaction solvent such as ethanol, at an appropriate temperature, usually at the boiling point of the solvent, in the presence of a base such as potassium hydroxide. The primary amino group of the isatin analog may be protected using a suitable protecting group, such as the trifluoroacetic acid amide. Acidification of the reaction mixture provides the carboxylic acid form of the desired compound 1.

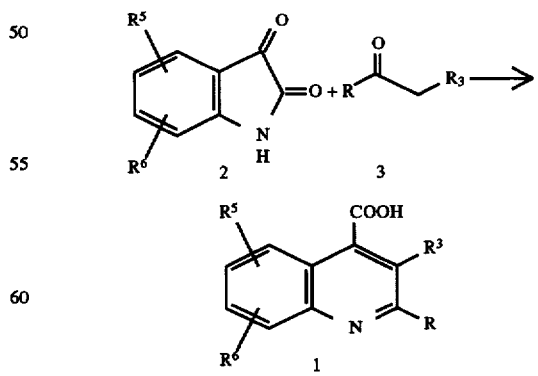

In some cases, substituents on the reactants may be protected using suitable protecting groups, such as a tert-butyl ether for protection of a phenolic hydroxyl group. In such cases, the protecting group is removed using standard methods after the condensation is carried out. The carboxylic acid may be converted to an appropriate salt using standard methods. The primary amine group in $R^6$ may be converted to a suitable acid addition salt, such as the hydrochloride salt, also using standard methods.

When any variable (for example, $R^1$ through $R^{10}$, m, n, P, X, Y, etc.) occurs more than one time in any constituent or in formula (I), or any other formula herein, its definition on each occurrence is independent of its definition at every other occurrence. Also, combinations of substituents and/or variables are permissible only if such combinations result in stable compounds.

As used herein and in the claims, "alkyl" is intended to include both branched and straight-chain saturated aliphatic hydrocarbon groups having the specified number of carbon atoms; "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl; and "bicycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Halogen" as used herein and in the claims refers to fluoro, chloro, bromo and iodo; and "counter-ion" is used to represent a small, negatively charged species such as chloride, bromide, hydroxide, acetate, sulfate and the like.

The term "substituted", as used herein and in the claims, means that any one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious hapten for the generation of antigenic immunogens or as tracer compounds.

As used herein and in the claims, "suitable salts" refer to derivatives of the disclosed compounds that are modified by making acid or base salts, or by modifying functional groups present in the compounds in such a way that the modifications are cleaved, either in routine manipulation or in vivo, to the parent compounds. Examples include, but are not limited to, mineral or organic acid salts of basic residues such as amines; alkali or organic salts of acidic residues such as carboxylic acids; and the like.

Suitable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., (1985), p. 1418, the disclosure of which is hereby incorporated by reference.

The preparation of representative haptens is shown in examples 1 through 4.

EXAMPLES

EXAMPLE 1

2-(2'-FLUORO-1,1'-BIPHENYL-4-YL)-3-METHYL-6-(2-AMINOETHYL)-4-QUINOLINECARBOXYLIC ACID 5-(2-trifluoroacetylaminoethyl)-isatin (572 mg, 2.0 mmol) and 4-(2-fluorophenyl)propiophenone (457 mg, 2.0 mmol) were suspended in ethanol (6 ml) and treated with a solution of KOH (1.01 g, 18.0 mmol) in water (3 ml). The mixture was heated at reflux for 48 hours. The mixture was then cooled, diluted with additional water, concentrated in vacuo to remove the ethanol, and filtered. The solid was washed with water, and the combined aqueous filtrate was adjusted to pH 8 with dilute aqueous HCl. The resulting solid was collected by filtration, rinsed thoroughly with water and dried to provide the title hapten as a cream-colored solid (500 mg, 62%): mp >250° C.; NMR ($CF_3COOD$) δ 8.61 (d, 1H), 8.44 (s, 1H), 8.33 (d, 1H), 8.12 (d, 2H), 7.95 (d, 2H), 7.69 (t, 1H), 7.57 (m, 1H), 7.43 (t, 1H), 7.35 (m, 1H), 3.92 (bs, 2H), 3.71 (bt, 2H), 2.95 (s, 3H); mass spec ($NH_3$-CI) m/z 401 (100%).

EXAMPLE 2

2-(2'-FLUORO-1,1'-BIPHENYL-4-YL)-3-METHYL-6-(2-AMINOETHYL)-4-QUINOLINECARBOXYLIC ACID, SODIUM SALT

A suspension of the product of Example 1 (100 mg) in methanol (10 ml) was treated with 1.0N aqueous NaOH (0.25 ml) and stirred at room temperature until a nearly homogeneous solution resulted. The solution was filtered and concentrated in vacuo. Residual water was removed by addition of toluene and concentration in vacuo. The title hapten was obtained as an off-white powder (106 mg, 100%): mp >250° C.

EXAMPLE 3

2-(2'-FLUORO-4'-HYDROXY-1,1'-BIPHENYL-4-YL)-3-METHYL-6-(2-AMINOETHYL)-4-QUINOLINECARBOXYLIC ACID

Using the same procedure as given in Example 1, 4-(2-fluoro-4-tert-butyloxyphenyl)propiophenone (901 mg, 3.0 mmol) was converted to 2-(2'-fluoro-4'-tert-butyloxy-1,1'-biphenyl-4-yl)-3-methyl-6-(2-aminoethyl)-4-quinolinecarboxylic acid (998 mg, 70%). Without purification, this material was stirred in trifluoroacetic acid (50 ml) at room temperature for 5 hours. The solution was poured into water (300 ml), and the pH was adjusted to 7.5 with aqueous NaOH. The suspension was filtered, and the collected solid was washed with water and dried to provide a pale yellow solid (873 mg). Chromatography on $C_{18}$-coated reversed-phase silica gel using 7:3 methanol-water as the eluent provided the title hapten (464 mg, 53%) as a pale yellowish solid: mp >250° C.; NMR ($CF_3COOD$) δ 11.6 (bs), 8.53 (d, 1H), 8.36 (s, 1H), 8.28 (d, 1H), 8.05 (d, 2H), 7.90 (d, 2H), 7.63 (t, 1H), 7.1-7.0 (2H), 3.89 (bt, 2H), 3.67 (bt, 2H), 2.94 (s, 3H); mass spec ($NH_3$-CI) m/z 417 (100%).

EXAMPLE 4

2-(2'-FLUORO-4'-HYDROXY-1,1'-BIPHENYL-4-YL)-3-METHYL-6-(2-AMINOETHYL)-4-QUINOLINECARBOXYLIC ACID, SODIUM SALT

Using the procedure of Example 2, the product of Example 3 (405 mg) was converted to the title hapten (425 mg, 100%): mp >250° C.

Additional haptens which may be prepared using the methods of Examples 1 through 4, or similar methods, are given in Table I. "Ph" in the tables designates phenyl.

TABLE I

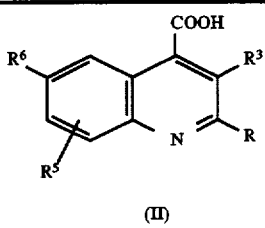

(II)

| Ex. | R | R³ | R⁵ | R⁶ |
|---|---|---|---|---|
| 5 | 4-Ph-Ph | methyl | H | $(CH_2)_2NH_2$ |
| 6 | 4-hexyl-Ph | methyl | H | $(CH_2)_3NH_2$ |
| 7 | 4-decyl-Ph | methyl | H | $(CH_2)_4NH_2$ |
| 8 | 4-hexenyl-Ph | methyl | H | $(CH_2)_5NH_2$ |
| 9 | 4-benzyl-Ph | methyl | H | $(CH_2)_6NH_2$ |
| 10 | 4-Phenoxy-Ph | methyl | H | $(CH_2)_8NH_2$ |
| 11 | 4-Ph-thio-Ph | methyl | H | $(CH_2)_{10}NH_2$ |
| 12 | 4-Ph-amino-Ph | methyl | H | $(CH_2)_{12}NH_2$ |
| 13 | 4-cyclohexyl-Ph | methyl | H | $(CH_2)_2NH_2$ |
| 14 | 5-Ph-2-furyl | methyl | H | $(CH_2)_2NH_2$ |
| 15 | 5-Ph-2-thienyl | methyl | H | $(CH_2)_2NH_2$ |
| 16 | 5-Ph-2-pyrryl | methyl | H | $(CH_2)_2NH_2$ |
| 17 | 4-Ph-2-fluoro-Ph | methyl | H | $(CH_2)_2NH_2$ |
| 18 | 4-(4-F-Ph)-Ph | methyl | H | $(CH_2)_2NH_2$ |
| 19 | 4-(3-Cl-Ph)-Ph | methyl | H | $(CH_2)_2NH_2$ |
| 20 | 5-Ph-2-pyridyl | methyl | H | $(CH_2)_2NH_2$ |
| 21 | 4-(4-Br-Ph)-Ph | methyl | H | $(CH_2)_2NH_2$ |
| 22 | 4-(3-Me-Ph)-Ph | methyl | H | $(CH_2)_2NH_2$ |
| 23 | 4-(3-NO_2-Ph)-Ph | methyl | H | $(CH_2)_2NH_2$ |
| 24 | 4-(4-MeO-Ph)-Ph | methyl | H | $(CH_2)_2NH_2$ |
| 25 | 4-(3-EtS-Ph)-Ph | methyl | H | $(CH_2)_2NH_2$ |
| 26 | 4-(3-CF_3-Ph)-Ph | methyl | H | $(CH_2)_2NH_2$ |
| 27 | 4-(4-NH_2-Ph)-Ph | methyl | H | $(CH_2)_2NH_2$ |
| 28 | 4(4-benxyloxy)-Ph | methyl | H | $(CH_2)_2NH_2$ |
| 29 | 4-Ph-Ph | H | H | $(CH_2)_2NH_2$ |
| 30 | 4-Ph-Ph | ethyl | H | $(CH_2)_2NH_2$ |
| 31 | 4-Ph-Ph | MeO | H | $(CH_2)_2NH_2$ |
| 32 | 4-Ph-Ph | MeS | H | $(CH_2)_2NH_2$ |
| 33 | 4-Ph-Ph | methyl | 5-F | $(CH_2)_2NH_2$ |
| 34 | 4-Ph-Ph | methyl | 7-Cl | $(CH_2)_2NH_2$ |
| 35 | 4-Ph-Ph | methyl | 5-CF_3 | $(CH_2)_2NH_2$ |
| 36 | 4-Ph-Ph | methyl | 7-CH_3 | $(CH_2)_2NH_2$ |
| 37 | 4-Ph-Ph | methyl | 7-CH_3S | $(CH_2)_2NH_2$ |
| 38 | 4-Ph-Ph | methyl | 7-C_2H_5 | $(CH_2)_2NH_2$ |
| 39 | 4-Ph-Ph | methyl | H | $CHMe(CH_2)_2NH_2$ |
| 40 | 4-Ph-SO-Ph | methyl | H | $(CH_2)_2NH_2$ |
| 41 | 4-Ph-SO_2-Ph | methyl | H | $(CH_2)_2NH_2$ |
| 42 | 4-Ph-Ph | methyl | 7-CH_3SO | $(CH_2)_2NH_2$ |

EXAMPLE 43

PREPARATION OF THE TRACER

The tracer compounds of the present invention are prepared by coupling a fluorescent moiety, preferably an analog of fluorescein, to a quinoline carboxylic acid, such as brequinar or a hapten of Formula (I). The fluorescent moiety can be linked to an amino group, for example that of $R^6$ in Formula (I), through an amide linkage using standard peptide coupling techniques in a suitable solvent. Standard peptide coupling techniques are known to those skilled in the art, and often utilize an N,N'-disubstituted carbodiimide and an additive such as N-hydroxysuccinimide, 1-hydroxybenzotriazole or p-nitrophenol. These additives form a stable but activated ester capable of reacting with an amino moiety. In addition, the peptide coupling techniques described in the example below can be used to couple a fluorescent moiety to a hapten of Formula (I) rather than the high molecular weight carrier molecule as described.

EXAMPLE 44

PREPARATION OF IMMUNOGEN

A. Using Glutaraldehyde as the Linker

An immunogen using the aminoethyl hapten of brequinar, 2-(2'-Fluoro-1,1'-Biphenyl-4-yl)-3-Methyl-6-(2-Aminoethyl)-4-Quinolinecarboxylic Acid, Sodium Salt, was prepared to raise antibodies which would be specific to brequinar. This hapten was conjugated to ovalbumin (hereinafter OA), bovine serum albumin (hereinafter BSA), and keyhole limpet hemocyanin (hereinafter KLH) using glutaraldehyde as the linker in a manner similar to that described in E. Harlow and D. Lane, ANTIBODIES a laboratory manual, Cold Spring Harbor, 1989, pg. 78–81. Briefly, equal volumes of 10 mg/ml OA, BSA, or KLH protein in phosphate buffered saline (PBS) and 5 mg/ml 2-(2'-Fluoro-1,1'-Biphenyl-4-yl)-3-Methyl-6-(2-Aminoethyl)-4-Quinolinecarboxylic Acid, Sodium Salt in PBS were mixed. A volume of 0.2% glutaraldehyde in PBS equal to the combined volume of the protein plus the 2-(2'-Fluoro-1,1'-Biphenyl-4-yl)-3-Methyl-6-(2-Aminoethyl)-4-Quinolinecarboxylic Acid, Sodium Salt was added slowly with mixing. For example, 0.2 ml protein plus 0.2 ml 2-(2'-Fluoro-1,1'-Biphenyl-4-yl)-3-Methyl-6-(2-Aminoethyl)-4-Quinolinecarboxylic Acid, Sodium Salt were mixed with 0.4 ml of 0.2% glutaraldehyde. The mixture was incubated at room temperature for at least one hour and was stopped by adding a quenching agent which flooded the reaction with primary amine groups. Glycine was used as a convenient source of primary amine. A volume of 1M glycine equal to ¼ the total reaction mixture was added and incubated at room temperature for at least one hour. For the example above, 0.2 ml of 1M glycine was used to quench the 0.8 ml reaction. The immunogens, 2-(2'-Fluoro-1,1'-Biphenyl-4-yl)- 3-Methyl-6-(2-Aminoethyl)-4-Quinolinecarboxylic Acid, Sodium Salt conjugated to protein, were separated from the smaller reactants using molecular sizing (desalting) columns; dialysis could have been used to achieve the same result. With the desalting columns, the immunogens were the first fractions off the column with significant Absorbance at 280 and 260 nm. The protein containing fractions were pooled for future use either for immunization or as reagents for the immunoassays.

B. Using Bis[2-(sulfosuccinimidooxycarbonyloxy)-ethyl] sulfone (sulfo-BSOCOES) as the linker 2-(2'-Fluoro-1,1'-Biphenyl-4-yl)-3-Methyl-6-(2-Aminoethyl)-4-Quinolinecarboxylic Acid, Sodium Salt was conjugated to OA, BSA, and KLH protein using sulfo-BSOCOES as the linking agent as described by D. A. Zarling et al., J. Immunol 124 (2), 913–920 (1980) which is hereby incorporated by reference. Two mg of protein was used per reaction in a volume of 0.4 ml PBS. 2-(2'-Fluoro-1,1'-Biphenyl-4-yl)-3-Methyl-6-(2-Aminoethyl)-4-Quinolinecarboxylic Acid, Sodium Salt in dimethyl sulfoxide (DMSO) (0.01 ml of 5 mg/ml) was added to the protein solution followed by addition of 0.01 ml of 100 mM sulfo-BSOCOES in DMSO. The reaction was incubated on ice for 30 min. with occasional shaking and then quenched with 0.1 ml of 1M glycine in PBS. The immunogens were isolated using the desalting columns as in the glutaraldehyde conjugation.

C. Using Disuccinimdyl Carbonate AS Linker

A stock solution of succinic anhydride was prepared by dissolving 24.3 mg in 1.635 ml of dimethylformamide (DMF). 2-(2'-Fluoro-1,1'-Biphenyl-4-yl)-3-Methyl-6-(2-Aminoethyl)- 4-Quinolinecarboxylic Acid, Sodium Salt (10 mg) was placed in a glass vial along with 161 μl succinic anhydride stock solution and 9 μl dry triethylamine. This was stirred overnight in the dark at room temperature. A stock solution of Disuccinimdyl carbonate (DSC) was prepared by dissolving 62.4 mg of DSC into 1.59 ml of dry DMF. 174 μl of the DSC stock and 9 μl of dry triethylamine were added to the 2-(2'-Fluoro-1,1'-Biphenyl-4-yl)-3-Methyl-6-(2-Aminoethyl)-4-Quinolinecarboxylic Acid, Sodium Salt-succinamic acid solution for activation. This was stirred for one hour in the dark at room temperature. Half of the activated 2-(2'-Fluoro-1,1'-Biphenyl-4-yl)-3-Methyl-6-(2-Aminoethyl)-4-Quinolinecarboxylic Acid, Sodium Salt-succinamic acid solution was rapidly added to either BSA or KLH solutions (26 mg protein dissolved in 43.3 ml of 0.15M sodium bicarbonate, pH 8.1) and gently agitated overnight in the dark at 4° C. After coupling, the immunogens were dialyzed against three changes of PBS to remove any free hapten and excess coupling reagents as described in *Chemistry of Protein Conjugation and Cross-Linking*, S. Wong, CRC Press, 1991, which is hereby incorporated by reference. Haptens were also conjugated to OA using this method.

An immunogen using the aminoethyl hapten of the inactive metabolite of brequinar, 2-(2'-Fluoro-4'hydroxy-1,1'-Biphenyl-4-yl)-3-Methyl-6-(2-Aminoethyl)-4-Quinolinecarboxylic Acid, Sodium Salt, was also prepared according to the methods described above to raise antibodies which would be specific to the inactive brequinar metabolite.

EXAMPLE 45

HYBRIDOMA AND MONOCLONAL ANTIBODY PREPARATION

Mice (6 week old Balb/C mice) were immunized by a single intraperitoneal or subcutaneous inoculation of 10, 50, or 100 μg per animal of an immunogen (as described above) in Complete Freund's Adjuvant (CFA). Three weeks later, each mouse was boosted with the same dose of immunogen in Incomplete Freund's Adjuvant (IFA). Tens days later, the mice were bled from the retroorbital plexus and the serum was tested for the presence of desired antibodies using an enzyme linked immunoassay (ELISA). The mouse with the highest antibody titer was challenged intraperitoneally with 100 μg immunogen in PBS and IFA, 4 and 3 days prior to the fusion as described in *Antibodies, A Laboratory Manual*, E. Harrow, D. Lane, Cold Spring Harbor Laboratory, 1989, which is hereby incorporated by reference.

The boosted mouse was sacrificed, the spleen removed, and somatic cell fusions were performed as follows. Splenocytes (1–4×10$^8$ cells) were fused with NS1 myeloma cells (ATCC TIB 18, P3/NS1/1-Ag4-1) in a ratio of 5-1, respectively, in the presence of 1 ml of 50% polyethylene glycol (1500) slowly added while stirring over a 1 min. period. Immediately after the fusion, the cells were resuspended in a total of 50 ml of Iscove's Modified DMEM containing hypoxanthine, thymidine, and aminopterin (HAT), and 15% fetal bovine serum (FBS), 2 mM glutamine, and 10 units/ml of IL-6 at 37° C. The diluted cells were plated into five 96-well tissue culture plates and incubated at 37° C. The cells were fed at days 1,2, and 3 following the fusion. Two weeks later hybridomas were detected and supernatants were collected for screening.

The screening of the monoclonal antibody supernatants was based on the ability to bind to hapten conjugated to OA and adsorbed onto 96-well microtitre plates. The plates were coated with 5 μg/ml of hapten-OA diluted in PBS and incubated overnight at 4° C. The wells were washed 3 times with PBS-Tween-20, blocked with 200 μl of 1% fish gelatin (can use BSA, instant milk, etc.) and incubated at room temperature for a minimum of 45 min. The wells were washed again 6 times and 100 μl of hybridoma supernatant was added to each well and incubated for 2 hr at room temperature. The wells were washed 6 times again and incubated for 1 hr at room temperature with 100 μl of alkaline phosphatase conjugated goat anti-mouse IgG diluted 1:3000 with PBS. The wells were washed again 6 times and 100 μl of substrate (1 p-nitrophenyl phosphate disodium tablet, 5 mg per 5 ml of 10% diethylamine) was added to each well. After color development, the absorbance was determined on a microplate reader at 405 nm.

Those antibodies displaying substantial activity by ELISA (greater than 3 times control media) were expanded and an aliquot frozen down. Five clones from fusion 1 and forty clones from fusion 2 showed positive results. Eight of these were cloned by limiting dilution.

To ensure isolation of a single monoclonal antibody producing cell, hybridomas were selected for subcloning by limiting dilution on the basis of differential reactivity by ELISA. A set of dilutions ranging from 20, 10, 5, 1, and 0.5 cells per well was prepared for each clone. 100 μl of a dilution was placed onto microtiter plates that had been seeded overnight with 100 μl mouse peritoneal macrophages as feeder cells. Sub-clones began appearing after 5 days and were screened by the ELISA method as described above. The re-cloning was repeated until five antibody producing single cell lines were isolated.

The clones were cultured in multiple tissue culture flasks and the antibody purified by passage through protein A/G agarose columns and elution with 0.2M glycine HCl, pH 2.5 elution buffer. The collected antibody was dialyzed against 20X volume of PBS and concentrated 3 to 4 fold.

The antibodies generated by the above method were subclassed using Sang Star isotyping kits and were determined to be IgG1. Total mouse IgG concentration was measured by mouse IgG ELISA and the specificity of each clone was determined by direct ELISA. These antibodies were also screened against the respective protein used for conjugation (i.e. BSA alone) and determined to have no cross reactivity.

EXAMPLE 46

POLYCLONAL ANTIBODY PREPARATION

Rabbits were immunized with 100 μg of immunogen in 2 ml Freund's complete adjuvant on day zero using multiple intradermal injections along the back. On day 14 the rabbits were boosted with 50 μg of immunogen in 2 ml Freund's incomplete adjuvant. The test bleed occurred on day 21. Production bleeds occurred weekly and boosts with 50 to 200 μg immunogen in Freund's incomplete adjuvant occurred monthly.

In one sequence rabbits were immunized with 2-(2'-Fluoro-1,1'-Biphenyl-4-yl)-3-Methyl-6-(2-Aminoethyl)-4-Quinolinecarboxylic Acid, Sodium Salt conjugated to either OA or KLH therefore the BSA-linked 2-(2'-Fluoro-1,1'-Biphenyl-4-yl)-3-Methyl-6-(2-Aminoethyl)-4-Quinolinecarboxylic Acid, Sodium Salt was used to detect the antibodies so that antibodies that cross-reacted with the carrier protein would not intefere with the analysis. 2-(2'-Fluoro-1,1'-Biphenyl-4-yl)-3-Methyl-6-(2-Aminoethyl)-4-Quinolinecarboxylic Acid, Sodium Salt-BSA was coated on 96-well EIA plates at concentrations of 10, 5, 2, and 1 μg/ml (0.1 ml/well). The coating was allowed to proceed overnight in the refrigerator in sealed plastic bags although in other instances coating of 1 to 2 hr at room temperature was sufficient. The EIA plates were washed (twice with 0.2 ml/well of PBS), blocked for 90 min. with 5% dry milk in PBS (0.2 ml/well) and washed (twice with 0.2 ml/well 0.05% Tween 20 in PBS followed by twice with 0.2 ml/well PBS). To the coated, washed, blocked, and washed EIA plates 0.1 ml/well aliquots of diluted antisera were added. Pre-bleed sera from the rabbits were evaluated at 1:50 dilution in PBS. Test bleed antisera were evaluated at 1:50, 1:500, and 1:5000 against each of the four amounts of 2-(2'-Fluoro-1,1'-Biphenyl-4-yl)-3-Methyl-6-(2-Aminoethyl)-4-Quinolinecarboxylic Acid, Sodium Salt-BSA. This allowed selection of rabbits with high titer of antibody and selection of a level of 2-(2'-Fluoro-1,1'-Biphenyl-4-yl)-3-Methyl-6-(2-Aminoethyl)-4-Quinolinecarboxylic Acid, Sodium Salt-BSA that gave a reasonable signal for future experiments. Some wells on the EIA plates were coated with OA, BSA, or KLH to detect antibodies against the carrier proteins and to insure that the rabbits did not have natural antibodies that cross-reacted with the BSA. The antisera were incubated on the EIA plates for 1 to 2 h followed by 1) washing (twice with 0.2 ml/well 0.05% Tween 20 in PBS followed by 0.2 ml/well PBS) and 2) the addition of 0.1 ml/well of an enzyme-linked secondary antibody. In this instance Goat anti-rabbit IgG - alkaline phosphatase (1:5000 dilution) was used but several commercial sources of enzyme-linked secondary antibody are available and suitable. After incubation with the secondary antibody for 1 to 2 h at room temperature or in some cases overnight in the refrigerator sealed in plastic bags, the EIA plates were washed (twice with 0.2 ml/well 0.05% Tween 20 in PBS followed by 0.2 ml/well PBS and finally 0.1 ml/well of the alkaline phosphatase buffer: 0.1 mM diethanolamine pH 9.5 with 0.5 mM $MgCl_2$) and incubated with 0.1 ml/well of substrate in this instance 1 mg/ml p-nitrophenylphosphate in 0.1 mM diethanolamine pH 9.5 with 0.5 mM $MgCl_2$ as suggested in Harlow and Lane p 597. The resulting color was measured at 405 nm using a microplate reader.

EXAMPLE 47

EVALUATION OF ANTIBODIES BY COMPETITION ASSAY

The monoclonal and polyclonal antibodies induced by immunizations with BSA- or KLH-2-(2'-Fluoro-1,1'-Biphenyl-4-yl)-3-Methyl-6-(2-Aminoethyl)-4-Quinolinecarboxylic Acid, Sodium Salt immunogens were tested in competition assays against OA- or BSA- 2-(2'-Fluoro-1,1'-Biphenyl-4-yl)-3-Methyl-6-(2-Aminoethyl)-4-Quinolinecarboxylic Acid, Sodium Salt. EIA plates were coated with 0.1 ml/well of 5 or 2 µg/ml OA- or BSA-2-(2'-Fluoro-1,1'-Biphenyl-4-yl)-3-Methyl-6-(2-Aminoethyl)-4-Quinolinecarboxylic Acid, Sodium Salt (as the antibody titre increased the amount of immunogen needed to coat the plate diminished). An antisera dilution was selected on the basis of trials to determine a dilution range where the color (A405) response was proportional to the amount of antisera added. Typically the polyclonal antisera were diluted 1:2000 to 1:4000 in PBS, while the monoclonal antibodies were used at 0.1 to 0.2 µg/ml in PBS. Brequinar was dissolved in PBS or rat plasma to demonstrate utility in a variety of matrices. Brequinar solutions and antibody solutions were mixed (0.1 ml/well, each) in 96-well 'low binding' plates and incubated 1 to 2 hr at room temperature prior to transfer to coated, blocked and washed EIA plates (as described above). The mixture was incubated on the EIA plates, which were previously blocked with the immunogen, for 2 h at room temperature, washed (as above) and incubated for 1 hr with an enzyme-linked secondary antibody to detect mouse (for monoclonal) or rabbit (for polyclonal) immunoglobins (as described above). In this instance, goat anti-mouse or goat anti-rabbit IgG alkaline phosphatase was used however, any other appropriate secondary antibody can be used. After washing to remove unbound secondary antibody, substrate (as described above) for alkaline phosphatase was added. The resultant color reaction was measured using a spectrophotometric EIA plate reader. Using this competition ELISA immunoassay, the polyclonal antibodies obtained were capable of detecting brequinar concentrations as low as 0.01 µg/ml in plasma; monoclonal antibodies obtained from the hybridomas described above were capable of detecting brequinar at concentrations as low as 1 ng/ml in plasma. Thus, antibodies of present invention will be useful to detect brequinar in clinical samples.

EXAMPLE 48

SPECIFICITY OF ANTIBODIES TO BREQUINAR

A further goal was to develop antisera and antibodies that could specifically distinguish between brequinar from the inactive hydroxyl metabolite that is formed naturally in the patient. The following experiments were used to demonstrate the ability of the specific antisera to distinguish brequinar from its inactive hydroxyl-metabolite and the potential to use these same antisera as tools to detect a pharmacologically active analog albeit at higher concentrations than for brequinar. Brequinar, its inactive hydroxyl-metabolite ("Inactive Metabolite", defined above), and a pharmacologically active analog ("Active Analog", defined above) were each diluted in rat plasma. The EIA plates were coated with 0.1 ml/well of 2 µg/ml 2-(2'-fluoro-1,1'-biphenyl-4-yl)-3-methyl-6-(2-aminoethyl)-4-quinolinecarboxylic acid, sodium salt-BSA immunogen for the polyclonals, or 2-(2'-fluoro-1,1'-biphenyl-4-yl)-3-methyl-6-(2-aminoethyl)-4-quinolinecarboxylic acid, sodium salt-OA immunogen for the monoclonals. The rat plasma containing diluted brequinar, analog, or metabolite and the antisera or monoclonal antibody were incubated together in polypropylene 96-well plates for 1-2 h at room temperature prior to transfer to the EIA plate, and were then incubated another 1-2 h. The appropriate secondary antibody (0.1 ml/well of Goat anti-rabbit IgG, or Goat anti-mouse IgG - alkaline phosphatase diluted 1:2000 in PBS) was incubated on the plate for 1 h. The A405 nm readings were taken at 20 to 40 min. after the addition of the alkaline phosphatase substrate. The following tables (II for polyclonal antibodies and III for monoclonal antibodies) give specificity and cross-reactivity information.

TABLE II

SPECIFICITY AND CROSS-REACTIVITY OF RABBIT ANTISERA TO BREQUINAR

| | (% cross-reactivity) | | | |
|---|---|---|---|---|
| Rabbit Antisera | Inactive Metabolite @ 1 µg/ml | Inactive Metabolite @ 0.1 µg/ml | Active Analog @ 1 µg/ml | Active Analog @ 0.1 µg/ml |
| A | 0.2% | <0.1% | 4% | 1% |
| B | 1% | <0.1% | 10% | 10% |

TABLE II-continued

SPECIFICITY AND CROSS-REACTIVITY OF RABBIT ANTISERA TO BREQUINAR

| Rabbit Antisera | Inactive Metabolite @ 1 µg/ml | Inactive Metabolite @ 0.1 µg/ml | Active Analog @ 1 µg/ml | Active Analog @ 0.1 µg/ml |
|---|---|---|---|---|
| | (% cross-reactivity) | | | |
| C | 0.3% | <0.1% | 6% | 8% |
| D | 0.1% | <0.1% | 2% | 1% |
| E | 0.2% | <0.1% | 5% | 3% |

TABLE III

SPECIFICITY AND CROSS-REACTIVITY OF MOUSE MONOCLONAL ANTIBODIES TO BREQUINAR

| MAb | Inactive Metabolite @ 1 µg/ml | Inactive Metabolite @ 0.1 µg/ml | Active Analog @ 1 µg/ml | Active Analog @ 0.1 µg/ml |
|---|---|---|---|---|
| | (% cross-reactivity) | | | |
| F | 0.3% | <0.1% | 0.8% | 2% |
| G | 0.6% | <0.1% | 2% | 9% |
| H | 0.8% | <0.1% | 3% | 9% |
| I | 0.4% | <0.1% | 0.8% | 1% |
| J | 0.3% | <0.1% | 2% | 6% |

These antibodies (both polyclonal antisera and monoclonal antibodies) are clearly able to distinguish between brequinar and its inactive hydroxyl-metabolite. For each of the antisera tested there was less than 1% cross reaction to the inactive metabolite. That is, at a concentration of 1.0 µg/ml, the inactive metabolite gave a signal equivalent to less than 0.01 µg/ml brequinar. Furthermore, some of the antisera have a reasonable ability to detect a pharmacologically active analog (8 to 10% cross-reactivity) and may be useful for detecting it and other active quinoline carboxylic acids.

The examples given here to demonstrate the utility of the invention were conducted using an ELISA format - antibody capture/antigen competition. However, this does not limit the utility of the invention to this format. To persons reasonably skilled in the art these monoclonal and polyclonal antibodies can be expected to be useful reagents for detecting quinoline carboxylic acids, including brequinar in clinical samples in formats mentioned above, such as (but not restricted to) radio immunoassay, fluorescence polarization immunoassay, chemiluminesence immunoassay, enzyme-multiplied immunoassay and other solid phase immunoassays.

Various modifications of the invention, such as by creating immunogens, and therefore antibodies, from haptens of formula (I) in addition to those shown and described herein will be apparent to those skilled in the art from the foregoing description. Such modifications are also intended to fall within the scope of the appended claims.

The foregoing disclosure includes all the information deemed essential to enable those of skill in the art to practice the claimed invention. Because the cited applications may provide further useful information these cited materials are hereby incorporated by reference in their entirety.

What is claimed is:

1. An immunogen comprised of a suitable high molecular weight carrier molecule, selected from the group consisting of proteins, polysaccharides, and latex particles, conjugated to a hapten of the Formula (I):

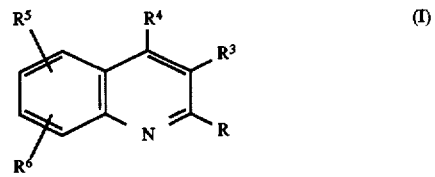

wherein:

R is

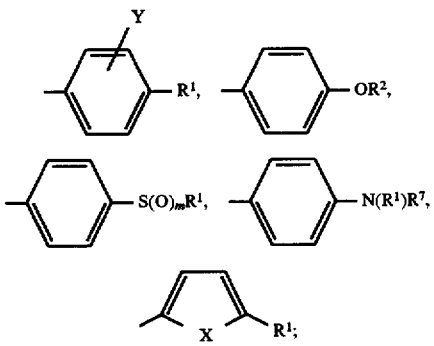

X is O, S, $NR^7$ or CH=N;

$R^1$ is alkyl of 5–12 carbon atoms, alkenyl of 5–12 carbon atoms, cycloalkyl of 3–7 carbon atoms, cycloalkylalkyl of 5–12 carbon atoms, phenyl substituted with 0–3 Y, or benzyl substituted with 0–3 Y;

$R^2$ is phenyl substituted with 0–3 Y, or benzyl substituted with 0–3 Y;

$R^3$ is H, alkoxy of 1–3 carbon atoms, alkylthio of 1–3 carbon atoms, or alkyl of 1–2 carbon atoms;

$R^4$ is COOH;

$R^5$ is H, F, Cl, Br, I, $CH_3$, $CF_3$, $S(O)_nR^8$ or ethyl;

$R^6$ is $(CR^9R^{10})_pCH_2NH_2$;

$R^7$, $R^8$, $R^9$ and $R^{10}$ are independently H or alkyl of 1–3 carbon atoms;

Y is selected independently at each occurrence from the group consisting of: H, F, Cl, Br, alkyl of 1–5 carbon atoms, $NO_2$, alkoxy of 1–5 carbon atoms, alkylthio of 1–5 carbon atoms, OH, $CF_3$ and $NH_2$;

m and n are independently 0, 1 or 2; and p is 0–12;

or a suitable salt form thereof.

2. An immunogen of claim 1 wherein the hapten is selected from the group consisting of:

2-(2'-Fluoro-1,1'-biphenyl-4-yl)-3-methyl-6-(2-aminoethyl)-4-quinolinecarboxylic acid;

2-(2'-Fluoro-1,1'-biphenyl-4-yl)-3-methyl-6-(2-aminoethyl)-4-quinolinecarboxylic acid, sodium salt;

2-(2'-Fluoro-4'-hydroxy-1,1'-biphenyl-4-yl)-3-methyl-6-(2-aminoethyl)-4-quinolinecarboxylic acid; and 2-(2'-Fluoro-4'-hydroxy-1,1'-biphenyl-4-yl)-3-methyl-6-(2-aminoethyl)-4-quinolinecarboxylic acid, sodium salt.

3. An immunogen of claim 1 wherein the protein molecule is selected from the group consisting of bovine serum albumin, ovalbumin, and keyhole limpet hemocyanin.

4. An immunogen of claim 2 wherein the protein molecule is selected from the group consisting of bovine serum albumin, ovalbumin, and keyhole limpet hemocyanin.

5. A tracer compound comprised of a hapten of Formula (I):

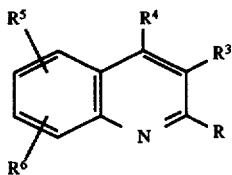

wherein:
R is

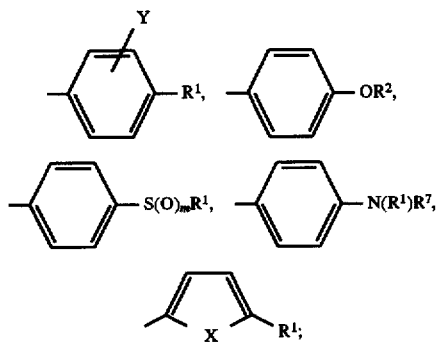

X is O, S, NR⁷ or CH=N;

R¹ is alkyl of 5–12 carbon atoms, alkenyl of 5–12 carbon atoms, cycloalkyl of 3–7 carbon atoms, cycloalkylalkyl of 5–12 carbon atoms, phenyl substituted with 0–3 Y, or benzyl substituted with 0–3 Y;

R² is phenyl substituted with 0–3 Y or benzyl substituted with 0–3 Y;

R³ is H, alkoxy of 1–3 carbon atoms, alkylthio of 1–3 carbon atoms, or alkyl of 1–2 carbon atoms;

R⁴ is COOH;

R⁵ is H, F, Cl, Br, I, $CH_3$, $CF_3$, $S(O)_nR^8$ or ethyl;

R⁶ is $(CR^9R^{10})_pCH_2NH_2$;

R⁷, R⁸, R⁹ and R¹⁰ are independently H or alkyl of 1–3 carbon atoms;

Y is selected independently at each occurrence from the group consisting of: H, F, Cl, Br, alkyl of 1–5 carbon atoms, $NO_2$, alkoxy of 1–5 carbon atoms, alkylthio of 1–5 carbon atoms, OH, $CF_3$ and $NH_2$;

m and n are independently 0, 1 or 2; and p is 0–12;

or a suitable salt thereof;

conjugated to a detectable fluorescent moiety.

6. A tracer compound of claim 5 wherein:

R is para-phenylene;

R¹ is cycloalkyl of 3–7 carbon atoms; phenyl optionally substituted with hydroxyl; phenyl substituted with one halogen, alkyl of 1–5 carbon atoms or $CF_3$ and also optionally with one hydroxyl; phenoxy; or phenoxy substituted with one halogen or alkyl of 1–5 carbon atoms;

R³ is H, alkyl of 1–2 carbon atoms or methylthio;

R⁵ is H, halogen, $CH_3$ or $CF_3$; and p is 1–12;

or a suitable salt thereof.

7. A tracer compound of claim 6 wherein:

R¹ is cyclohexyl, phenyl, hydroxyphenyl, fluorophenyl, fluorohydroxyphenyl, or methylphenyl;

R⁵ is hydrogen; and

R⁶ is $(CH_2)_pNH_2$, and is located at the 6-position of the quinoline ring; and p is 2–8.

8. A tracer compound of claim 7 selected from the group consisting of:

2-(2'-Fluoro-1,1'-biphenyl-4-yl)-3-methyl-6-(2-aminoethyl)-4-quinolinecarboxylic acid;

2-(2'-Fluoro-1,1'-biphenyl-4-yl)-3-methyl-6-(2-aminoethyl)-4-quinolinecarboxylic acid, sodium salt;

2-(2'-Fluoro-4'-hydroxy-1,1'-biphenyl-4-yl)-3-methyl-6-(2-aminoethyl)-4-quinolinecarboxylic acid; and 2-(2'-Fluoro-4'-hydroxy-1,1'-biphenyl-4-yl)-3-methyl-6-(2-aminoethyl)-4-quinolinecarboxylic acid, sodium salt.

9. A tracer compound of claim 5 wherein said detectable fluorescent moiety is selected from the group consisting of chemiluminescent molecules, luminescent molecules and enzyme molecules.

10. A tracer compound of claim 6 wherein said detectable fluorescent moiety is selected from the group consisting of chemiluminescent molecules, luminescent molecules and enzyme molecules.

11. A tracer compound of claim 7 wherein said detectable fluorescent moiety is selected from the group consisting of chemiluminescent molecules, luminescent molecules and enzyme molecules.

12. A tracer compound of claim 8 wherein said detectable fluorescent moiety is selected from the group consisting of chemiluminescent molecules, luminescent molecules and enzyme molecules.

13. A tracer compound of claim 9 wherein said luminescent molecules are fluorescein molecules or analogs thereof.

14. A tracer compound of claim 10 wherein said luminescent molecules are fluorescein molecules or analogs thereof.

15. A tracer compound of claim 11 wherein said luminescent molecules are fluorescein molecules or analogs thereof.

16. A tracer compound of claim 12 wherein said luminescent molecules are fluorescein molecules or analogs thereof.

17. A tracer compound of claim 13 wherein said fluorescein molecules or analogs thereof are selected from the group consisting of aminomethylfluoresceins, carboxyfluoresceins, and fluoresceinamines.

18. A tracer compound of claim 13 wherein said fluorescein molecules or analogs thereof are selected from the group consisting of aminomethylfluoresceins, carboxyfluoresceins, and fluoresceinamines.

19. A tracer compound of claim 13 wherein said fluorescein molecules or analogs thereof are selected from the group consisting of aminomethylfluoresceins, carboxyfluoresceins, and fluoresceinamines.

20. A tracer compound of claim 13 wherein said fluorescein molecules or analogs thereof are selected from the group consisting of aminomethylfluoresceins, carboxyfluoresceins, and fluoresceinamines.

* * * * *